US010709896B2

(12) United States Patent
Neuberger et al.

(10) Patent No.: US 10,709,896 B2
(45) Date of Patent: Jul. 14, 2020

(54) SYSTEM AND METHOD FOR TREATING HEMORRHOIDS

(75) Inventors: Wolfgang Neuberger, Dubai (AE); Endrick Groenhoff, Bonn (DE)

(73) Assignee: Biolitec Unternehmensbeteiligungs II AG, Vienna (AT)

( * ) Notice: Subject to any disclaimer, the term of this patent is extended or adjusted under 35 U.S.C. 154(b) by 336 days.

(21) Appl. No.: 12/976,484

(22) Filed: Dec. 22, 2010

(65) Prior Publication Data

US 2012/0004546 A1 Jan. 5, 2012

Related U.S. Application Data

(60) Provisional application No. 61/288,993, filed on Dec. 22, 2009.

(51) Int. Cl.
| *A61N 5/06* | (2006.01) |
| *A61B 8/12* | (2006.01) |
| *A61N 5/067* | (2006.01) |
| *A61B 8/00* | (2006.01) |

(52) U.S. Cl.
CPC .............. *A61N 5/0603* (2013.01); *A61B 8/12* (2013.01); *A61B 8/4461* (2013.01); *A61N 2005/0602* (2013.01); *A61N 2005/063* (2013.01); *A61N 2005/067* (2013.01); *A61N 2005/0612* (2013.01); *A61N 2005/0644* (2013.01); *A61N 2005/0659* (2013.01)

(58) Field of Classification Search
USPC ....................................................... 600/439
See application file for complete search history.

(56) References Cited

U.S. PATENT DOCUMENTS

| 4,672,963 | A | * | 6/1987 | Barken | ........................... | 606/12 |
| 5,377,683 | A | * | 1/1995 | Barken | ........................ | 600/439 |
| 5,703,985 | A | * | 12/1997 | Owyang | ....................... | 385/117 |
| 5,916,210 | A | * | 6/1999 | Winston | ................... | A61B 8/12 |
| | | | | | | 600/439 |
| 5,967,984 | A | * | 10/1999 | Chu et al. | ...................... | 600/439 |
| 6,200,311 | B1 | * | 3/2001 | Danek et al. | ................... | 606/15 |
| 6,419,683 | B1 | * | 7/2002 | Burgard | ........................ | 606/169 |
| 7,118,528 | B1 | * | 10/2006 | Piskun | .......................... | 600/105 |

(Continued)

*Primary Examiner* — Bill Thomson
*Assistant Examiner* — Shahdeep Mohammed
(74) *Attorney, Agent, or Firm* — BJ. Associates; Bolesh J. Skutnik

(57) ABSTRACT

System and method for treating hemorrhoidal piles, addressing both cause and symptoms, by endoluminal/interstitial application of energy are disclosed. The dilated blood arteries in anal/rectal region are irradiated from inside the pile using (laser) energy for minimal pain/discomfort. The center of the pile is irradiated over a certain diameter, absorbing energy; and is denatured causing volume reduction. Central vessels located in the same diameter are obliterated immediately, relieving bleeding. During treatment, new connective tissue replaces the coagulated tissue. Closing inflowing arteries further shrinks piles in weeks to three months. Complications are highly diminished. A hand-piece and a fiber with a sharp distal tip are beneficial. Including an imaging system, (ultrasound imaging, optical coherence tomography) and an intelligent system to calculate necessary laser energy parameters help address each pile individually.

15 Claims, 5 Drawing Sheets

(56) References Cited

U.S. PATENT DOCUMENTS

| | | | |
|---|---|---|---|
| 2002/0133077 A1* | 9/2002 | Edwardsen | A61B 1/00177 600/462 |
| 2006/0167473 A1* | 7/2006 | Scheyer | 606/139 |
| 2007/0118108 A1* | 5/2007 | Croft | 606/41 |
| 2007/0293726 A1* | 12/2007 | Goldfarb | A61B 1/0014 600/178 |
| 2008/0091104 A1* | 4/2008 | Abraham | A61B 8/0841 600/439 |
| 2008/0281204 A1* | 11/2008 | Salfi et al. | 600/454 |
| 2009/0012369 A1* | 1/2009 | Robinson | A61B 1/00009 600/182 |
| 2010/0228119 A1* | 9/2010 | Brennan et al. | 600/424 |

\* cited by examiner

SYSTEM AND METHOD FOR TREATING HEMORRHOIDS

DOMESTIC PRIORITY UNDER 35 USC 119(e)

This application claims the benefit of U.S. Provisional Application Ser. No. 61/288,993 by Endrik Groenhoff and Wolfgang Neuberger, entitled "System and Method for Treating Hemorrhoids" filed Dec. 22, 2009, which is incorporated by reference herein.

BACKGROUND OF THE INVENTION

1. Field of the Invention

The present invention relates to a system and method for treating hemorrhoids in a patient using a minimally invasive method. In particular it provides a method and a system for treating hemorrhoidal cushions by using laser technology.

2. Information Disclosure Statement

Hemorrhoids are dilated or bulging veins of the rectum and anus, caused by increased pressure in the rectal veins, resulting in bleeding, itching and pain. Pressure caused on the walls of the rectum weakens the muscles that support the hemorrhoidal vessels. These vessels then become enlarged and lose their support forming a sac-like protrusion inside the rectal canal, referred to as internal hemorrhoids or under the skin around the anus, called external hemorrhoids. When internal hemorrhoids push out of the anal opening, it is referred to as prolapsed hemorrhoids. Sometimes, blood clotting or thrombus is seen in external hemorrhoids; this condition is called a thrombosed external hemorrhoid. Hemorrhoids can occur at any time in all age groups and in both sexes. They are most common among adults ages 45 to 65. Hemorrhoids are also common in pregnant women.

The arteries supplying blood to the anal canal descend into the canal from the rectum above and form a rich network of arteries that communicate with each other around the anal canal. Because of this rich network of arteries, hemorrhoidal blood vessels have a ready supply of arterial blood. The blood vessels that supply the hemorrhoidal vessels pass through the supporting tissue of the hemorrhoidal cushions. The anal veins drain blood away from the anal canal and the hemorrhoids. These veins drain in two directions. The first direction is upwards into the rectum, and the second is downwards beneath the skin surrounding the anus. The suggestion based on earlier theories for hemorrhoid aetiology is that a local increase in venous pressure causes dilation of the hemorrhoid plexus within the anal cushions. This theory is refuted now based on recent studies of the vascular anatomy of the anal cushion.

Most common symptoms of hemorrhoids are bleeding and prolapse at defecation. Thrombosis and anal fissure cause pain. Other symptoms include soiling, itching or perianal irritations.

For moderate hemorrhoid conditions, there are numerous existing treatments, whose main objectives are to alleviate symptoms or to help avoid aggravation of the hemorrhoid condition. For instance, ointments, special diets, patches and hemorrhoid massage, which is used to stimulate blood flow in the treatment area.

A conventional treatment method is anal dilation, wherein the anal sphincter muscle is stretched or dilated to prevent hemorrhoids from increasing rectal pressure, as well as reduce the straining while passing stool. Potential side effects of this procedure are fecal incontinence or anal leakage. Furthermore, this method cannot be used in the older age group with weak sphincter muscles.

In rubber-band ligation methods, a special rubber band is tied around internal mucosa above the dentate line. The band lifts the hemorrhoids below and cuts off blood circulation to the hemorrhoid. Within a week, the necrotic tissue will shrivel and fall off along with the band. In the case of multiple hemorrhoids, each is treated separately about one month apart. Common side effects of these methods include complications such as clotting of external hemorrhoids and bleeding.

In Doppler-guided ligation methods, a specially adapted proctoscope with an incorporated Doppler probe is used to ligate hemorrhoid arteries. The Doppler probe is inserted and used to locate the hemorrhoid arteries by audible alteration of signal. Once located, a needle holder is inserted into the lumen of the proctoscope and the artery is ligated with an absorbable suture into the submucosa. The procedure is repeated. Doppler-guided ligation of the hemorrhoid artery disrupts the arterial inflow and tethers the mucosa, causing the hemorrhoidal mass to shrink and retract. Currently this procedure is carried out under general anesthesia and few patients are able to tolerate it under simple sedation.

Sclerotherapy or injection therapy involves injecting a sclerosing or hardening agent into the base of the internal hemorrhoids. The sclerosing agent causes the vein walls to collapse and the hemorrhoids to shrivel up. This method can be used for treating multiple hemorrhoids at once and is more often used for treating older men and women with fragile veins. Sometimes abscesses are reported in patients.

Cryosurgery or freezing methods use liquid nitrogen or nitrous oxide to cool the cryoprobe to freezing temperatures. The frozen tip of the probe is then applied to the hemorrhoid to freeze and destroy the tissue. Two or three weeks later, the hemorrhoids will shrink and fall off. Both internal and external hemorrhoids can be treated by this method. This method is very painful and other complications include foul odor from discharge of treated hemorrhoids lasting for about a week, requiring use of absorbent pads. The open wound can also become infected.

Hemorrhoidectomy is a surgical method of removing hemorrhoids, usually done in severe cases. It is recommended for prolapsed or thrombosed internal hemorrhoids, or large and painful external ones. In this method, hemorrhoids are cut off using scalpels or a laser, the cut sewn up with stitches, and a small pad placed in the anus to absorb discharge from the region. This method requires anesthesia and hospitalization for a few days and patient must stay on sick leave for up to several weeks. This is therefore a very expensive method. Side effects can include severe pain, bleeding, narrowing of anal canal which may lead to anal fisures, inability to defecate and scarring.

Electric treatments of hemorrhoids apply an electric current directly into the deficient vein. Electric current, either negative or positive, causes a chemical or thermal reaction within the tissue that either destroys and/or obliterates the hemorrhoid. Examples of these treatments include bipolar electrotherapy and hemorrhoidolysis, in which therapeutic galvanic waves are applied directly to the hemorrhoid, producing a chemical reaction that shrinks and dissolves hemorrhoidal tissue. These treatments are limited to only internal hemorrhoids. Furthermore, they are time-consuming treatments, tedious for physician and patient, and may lead to anorectal fistula development.

Another method using laser energy for treating hemorrhoids has been proposed by Salfi et al. in U.S. Patent Publication 2008/0281204, which presents a system and method for treating branches of the superior hemorrhoidal artery by photocoagulation using laser energy. The treatment system photocoagulates the branches of superior hemorrhoidal artery in the anal and rectal regions using laser energy while causing minimal pain or discomfort to the patient. The post operative recovery is faster than alternative approaches with no complications. Anesthesia is no longer required, as it is in most other successful methods, greatly reducing complications and simplifying the treatment. This method can be successfully used in grade one and two hemorrhoids. Nevertheless, grade three hemorrhoids treatment may not be feasible with this technique by itself. Furthermore, shrinkage and retraction usually occurs some days after surgery, thus symptom relief can be delayed.

Plapler (See Photomedicine and Laser Surgery Volume 26, Number 2, 2008, Pp. 143-14 A New Method for Hemorrhoid Surgery: Experimental Model of Diode Laser Application in Monkeys) has published an experimental method of endovascular laser therapy for treating hemorrhoids using diode laser application to monkeys in which hemorrhoids were induced by ligation of the inferior hemorrhoidal vein. Laser energy was delivered to the surrounding submucosal interstitial tissue, reducing the hemorrhoids. A recent new method which consists in attacking the cushions in humans directly by submucosal delivery of laser energy is exposed by Karahaliloglu (See: Coloproctology 29, 2007, Nr. 6© Urban & Vogel. First Results after Laser Obliteration of First- and Second. Degree Hemorrhoids). Laser energy provides submucous obliteration with subsequent fibrotic tissue change of the hemorrhoidal vascular convolute. Performed without anesthesia, treatment leads to unpleasant pain sensations, so it is routinely carried out with application of 1 ml local anesthetic per knot, whereby all patients are pain free during treatment. This method has had high patient acceptance and satisfaction when performed properly. However, procedure is sometimes difficult to carryout due to bleeding of treated piles. Furthermore, although results are satisfactory regarding relief in a short period of time by direct shrinking of the hemorrhoidal cushion, this method does not attack the main cause of hemorrhoid formation. Additionally it may not be suitable for larger hemorrhoidal piles and therefore recurrence is probable over time.

Hence there remains a need for developing a suitable device and method for treating hemorrhoids using minimal invasive methods which can overcome or minimize the drawbacks reported in the above treatment methods. This should be achieved by reducing the dimensions of the hemorrhoidal cushion(s) preserving their function of fine continence, and to completely spare the sensible anodermal skin and the mucosa to reduce pain and wound circumference and to reduce patient inactivity time periods. Present invention addresses these needs.

OBJECTIVES AND BRIEF SUMMARY OF THE INVENTION

It is an objective of the present invention, to provide a laser treatment system for treating hemorrhoids in patients.

It is a further objective of the present invention, to provide a method of treating hemorrhoids by shrinking hemorrhoidal cushions from the inside.

It is another objective of the present invention to provide a treatment method that spares the sensible anodermal skin from cutting or sewing, by means of applying laser energy into the piles themselves.

It is another objective of the present invention to provide a treatment method that leaves the mucosal surface as well as the sphincter in good condition by means of applying laser energy in a controlled way into the hemorrhoidal piles themselves.

Briefly stated the present invention is a system and method for treating hemorrhoidal piles by endoluminal/interstitial application of energy. The inflamed dilated blood vessel compounds in and around the anal region, often called hemorrhoids or piles, are caused by a connective tissue disorder, a relative increase in pressure in the superior hemorrhoidal artery and weakening of the vessels' valves. A suitable treatment system and method are provided, herein, for treating such conditions in a minimally invasive manner. The treatment method disclosed consists in irradiating the dilated blood arteries in the anal and rectal regions from the inside of the pile using (laser) energy in a very controlled manner while causing minimal pain or discomfort to the patient. As a result, the center of the pile is illuminated for a certain diameter and, by the absorption of the energy, denatured causing a volume reduction. Additionally, the central vessels located within that diameter are obliterated in order to close them for accomplishing immediate relief of (bleeding) symptoms. As a consequence of treating the piles, new connective tissue replaces the coagulated tissue and due to the closing of the inflowing arteries, the piles shrink further over a time of several weeks up to three months. Bleeding and other complications are highly diminished. The treatment system is provided with an optical fiber which features means for distributing the energy such that at a front end or radial tip or a combination of these, illumination is enabled. The optical fiber can be placed in a hand-piece for better guidance during the procedure. The optical fiber may feature a sharp distal tip to enable injection of the optical fiber through the mucosa or perianal skin. In a preferred embodiment, device includes an imaging system such as ultrasound imaging or optical coherence tomography, and an intelligent system capable of measuring different geometrical parameters and calculating the necessary laser energy parameters needed to address every pile individually. The hemorrhoids are thus treated integrally, since both cause and symptoms are addressed and results are obtained within a short period of time.

The above and other objects, features and advantages of the present invention will become apparent from the following description read in conjunction with the accompanying drawings.

DETAILED DESCRIPTION OF PREFERRED EMBODIMENTS

Hemorrhoids or as commonly called piles, when visible, are conditions found to occur in affected veins in and around the anal or rectal areas. It is a condition found to affect 30% of the general population.

The arteries supplying blood to the anal canal descend into the canal from the rectum above and form a rich network of arteries that communicate with each other around the anal canal. Because of this rich network of arteries, hemorrhoidal blood vessels have a ready supply of arterial blood. The blood arteries that supply the hemorrhoidal vessels pass through the supporting tissue of the hemorrhoidal cushions. The anal veins drain blood away from the anal canal and the hemorrhoids. These veins drain in two directions. The first direction is upwards into the rectum, and the second is downwards beneath the skin surrounding the anus. The suggestion, based on earlier theories for hemorrhoid etiology, is that a local increase in venous pressure causes dilation of the hemorrhoid plexus within the anal cushions. That theory is now refuted, based on recent studies of the vascular anatomy of the anal cushion.

Despite their vascular appearance and tendency to bleed, the development of hemorrhoids is believed due to a connective tissue disorder and an absolute or relative increased blood flow from the superior hemorrhoidal artery. Arteriovenous anastomoses within the submucosa are thought to contribute to the increase in volume of the anal cushions. This arterial component explains why hemorrhoidal bleeding has the appearance and pH of arterial blood. On the other hand, patient symptoms occur mainly at anal cushions. Based on cause and effect of development of hemorrhoids, a new treatment system and method is proposed.

Figure 1:
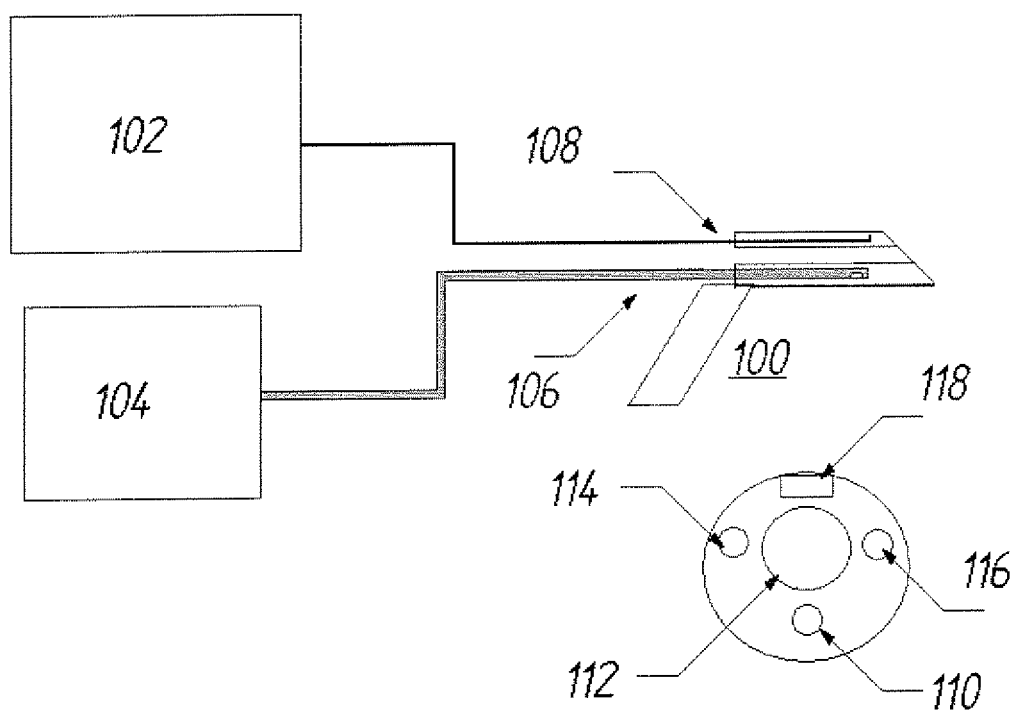
FIG. 1 is a schematic representation of treatment system having disposable or reusable anoscope and fiber optics.

In the present invention, a new treatment method and a system is provided for treating a hemorrhoid condition based on the new theories of hemorrhoidal etiology and on patient symptoms. Here, laser energy is used to shrink the hemorrhoidal mass and to obliterate the feeder arteries which supply the hemorrhoids and then to irradiate piles in order to achieve patient's immediate relief from symptoms. Ultrasound imaging, Doppler ultrasound or optical coherence tomography can be used to initially identify and locate arteries, and after lasing to assess treatment effectiveness. Piles are treated directly by submucosal delivery of laser energy, thereby shrinking them. Power is applied to every knot in an oral-aboral way to obtain a collagen melting and shrinking of the arteriovenous and connective tissue that fills the submucosal layers. Appropriate anesthesia should be used. The treatment device is provided with a disposable or reusable anoscope and other components. The appropriately sized anoscope can internally be provided with channels for introducing the treatment components. The components of the treatment system 100 are schematized in FIG. 1 and include laser source 102, and ultrasound imaging system or Doppler system 104. Ultrasound probe 106 is used to identify and position the scope's distal end to treat the branching hemorrhoidal arteries. Optical fiber 108 transmits laser energy from laser source 102 to target hemorrhoidal cushions. The system includes an optical fiber with means for adapting illumination of target area. In another embodiment, the optical fiber is guided with the help of a handpiece. In another embodiment, the handpiece features scaling to enable defined treatment or application of radiation per unit of length. In another embodiment the system includes two channels, one 110 for optical fiber 108 and another 112 for ultrasound probe 106. In another embodiment, the system may include channels for aspirating means 114 to remove exhaust fumes, heat, fluids or blood, as well as a channel for a light source 116 for illuminating the field. It may also include viewing window 118.

Figure 2:
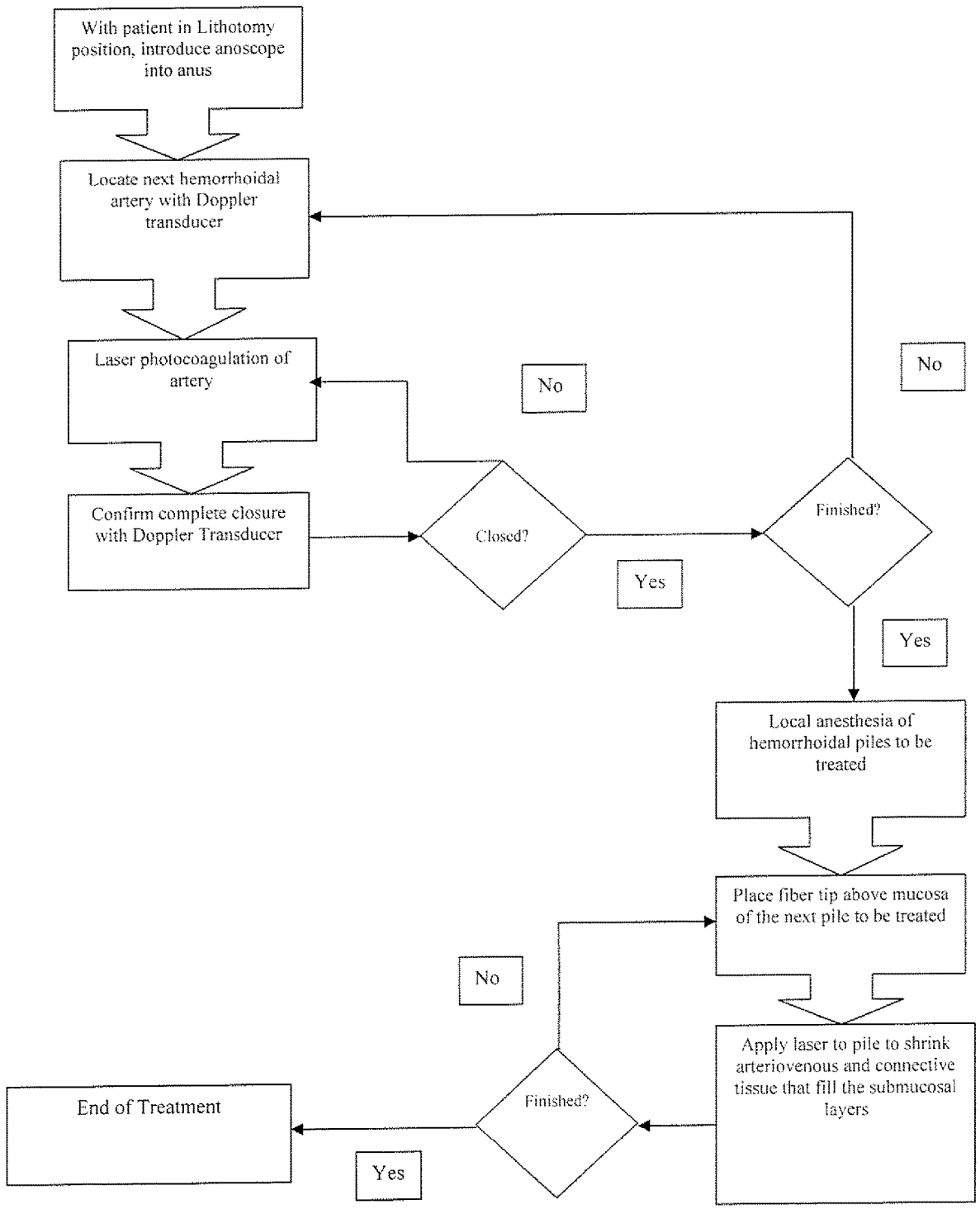
FIG. 2 depicts a flow diagram showing main steps carried out in disclosed method.

In a preferred embodiment, depicted in FIG. 2, a schematic representation of treatment system's main steps is presented. The method of treating the hemorrhoidal cushions using the treatment system in general involves inserting anoscope, with patient in lithotomy position, into the anal canal above the hemorrhoidal cushions and irradiating the piles with laser energy. The branches of hemorrhoidal arteries are located by a Doppler transducer or other methods known in the art. After locating the vessels, laser energy is applied to the artery branches using an optical fiber which is introduced into and/or around the artery a few centimeters from the skin line. The laser irradiation leads to photocoagulation of hemorrhoidal artery branches. The complete closure is confirmed by Doppler. Once this procedure is completed, patient is kept in lithotomy position and proctoscope is maintained inside anus. Under local anesthesia, fiber tip is placed on the mucosa of the hemorrhoidal knot to be treated and the laser is activated while entering the mucosa. After that, proper placing of the fiber into the base of the hemorrhoidal cushion is arranged. Using the aiming beam and digital control, the proper location of the tip can be controlled accurately to prevent from positioning it too deeply or too superficially to spare the sphincter and the mucosa. Once positioned, laser power is applied to every knot in an oral-aboral way to obtain collagen melting and shrinking of the arteriovenous and connective tissue that fills the submucosal layers. Then, remaining knots are treated by repositioning optical fiber. Previous to repositioning, fiber should be pulled back to prevent sliding of the tissue and application of energy to the same cushion. Lasing parameters should be adapted to the size of the knot/pile. If necessary, the same penetration opening can be used to repeat insertion and treatment in a spreading motion. Bigger knots must retain higher levels of energy whilst small knots only receive low doses. An appropriate wavelength must be chosen so that depth of laser/tissue interaction is about 5 mm. For example, 980 nm or 1470 nm may be used.

In some cases it may be necessary to penetrate trough the perianal skin to treat the entire length of the hemorrhoid, especially in cases in which hemorrhoidal extension lifts the anoderm or grows underneath.

As real-time ultrasound guidance can be used in this procedure, muscle necrosis is practically avoided, since laser energy is not applied close to the sphincter or mucosa. Although the knots shrink instantly, the successive tissue processes start several days after procedure. At times, if pile is too large, two options are possible and may vary according to patient's expectations and physician's criteria. One option is to shrink pile further in a second and, if necessary, a third session to obtain the desired result. The other option is to surgically remove remaining pile; this procedure is rendered much simpler thanks to diminished bleeding due to previous artery photocoagulation and pile obliteration.

The method accomplished by hemorrhoidal treatment described in present invention has many advantages when compared to other treatment methods. Use of the appropriately specially designed anoscope is relatively painless and causes less discomfort to the patient when inserted into the anal opening.

If necessary, general anesthesia, spinal or epidural anesthesia can be used for maximum patient comfort.

The procedure is easy to carry out and can be performed in a few minutes with minimal post-operative pain. During the procedure, position of the optical fiber can be monitored using Doppler. This also prevents damaging other normal vessels in the rectal and anal regions. Complete closure of each damaged artery is confirmed by ultrasound. Furthermore, subsequent steps are rendered easier as bleeding is eliminated or substantially reduced. Thus, pile irradiation causes little or no bleeding due to previously ligation or photocoagulation of terminal branches of hemorrhoidal arteries. Irradiation of pile causes submucosal obliteration with subsequent fibrotic tissue change of the hemorrhoidal vascular convolute. In other words they disappear within a short time. This makes treatment complete, as both the cause and the symptoms of hemorrhoidal piles are attacked and eliminated in one procedure.

Figure 3A:
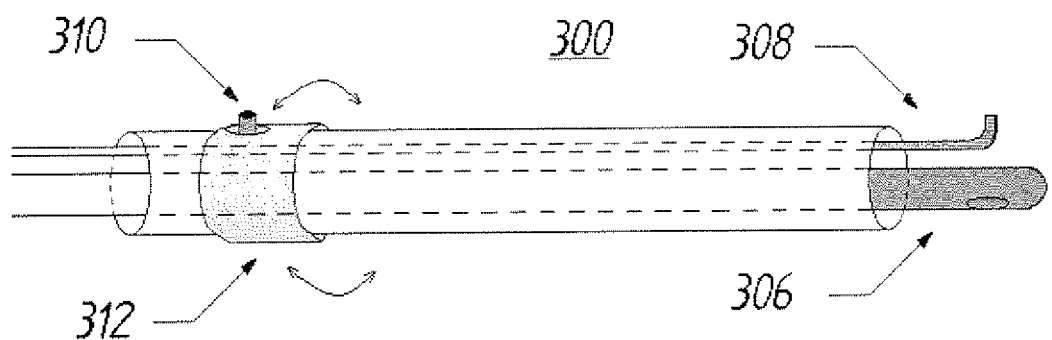
FIGS. 3a and 3b show a preferred embodiment in which special handpiece has a rotational mechanism for switching positions between optical fiber and a ultrasound probe.
Figure 3B:
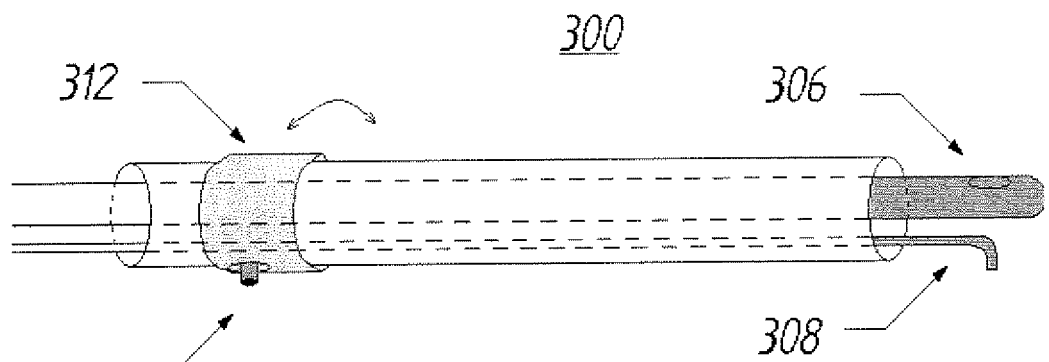

In a preferred embodiment, shown in FIGS. 3a and 3b, a special handpiece 300 is used with at least two insertion channels, in which both ultrasound probe 306 and optical fiber 308 can be inserted together. Furthermore, handpiece 300 has a rotational mechanism such that ultrasound probe 306 and optical fiber 308 can be rotated 180 degrees and therefore switch places. For example, in the method disclosed in present invention, handpiece 300 is inserted into anus with Doppler probe 306 and optical fiber 308 in place. Then, Doppler probe 306 is put in place to search for hemorrhoidal artery. Optical fiber 308 is thus on the opposite end. Once hemorrhoidal artery is detected by ultrasound probe 306, handpiece 300 is rotated 180 degrees so optical fiber 308 moves to exact position in which blood flow was detected and hemorrhoidal artery can be precisely photocoagulated. Then, rotation is repeated so ultrasound probe 306 can confirm effective photocoagulation of hemorrhoidal artery. The next step described in present invention is to directly attack hemorrhoidal cushions. This can be carried out without removing handpiece 300 from anus, so physician does not need to take probe 306 or fiber 308 out until entire procedure is over. This makes treatment shorter, as less maneuvering involving insertion and removal of treatment elements is necessary. Furthermore, precision is enhanced, since the system assures a perfect switch between ultrasound probe 306 and laser fiber 308, thus irradiation is applied in the exact desired place. Switching movement is achieved by pressing button 310 and turning grip 312, and then the mechanism is locked in place by releasing button 310.

Figure 4A:
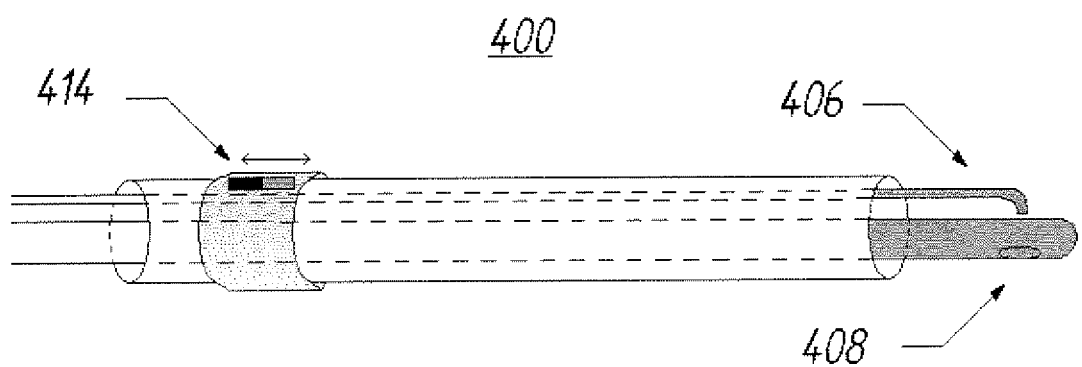
FIGS. 4b and 4b show a preferred embodiment in which a special handpiece has a sliding mechanism for changing relative positions of optical fiber and ultrasound probe along main axis.
Figure 4B:
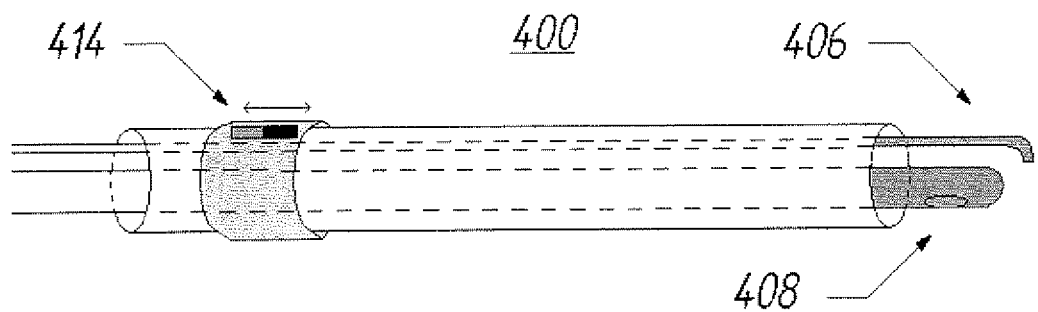

In another embodiment, depicted in FIGS. 4a and 4b, handpiece has a longitudinal sliding movement mechanism 414. So, for example, probe 406 and fiber 408 can be inserted facing the same direction. After detecting hemorrhoidal artery, ultrasound probe 406 can be moved back with respect to fiber 408 instead of rotating to switch places and lasing can be carried out without danger of probe 406 being damaged by laser energy emitted from optical fiber 408. Thus, after locating hemorrhoidal artery, photocoagulation step follows by merely sliding back ultrasound probe.

Figure 5:
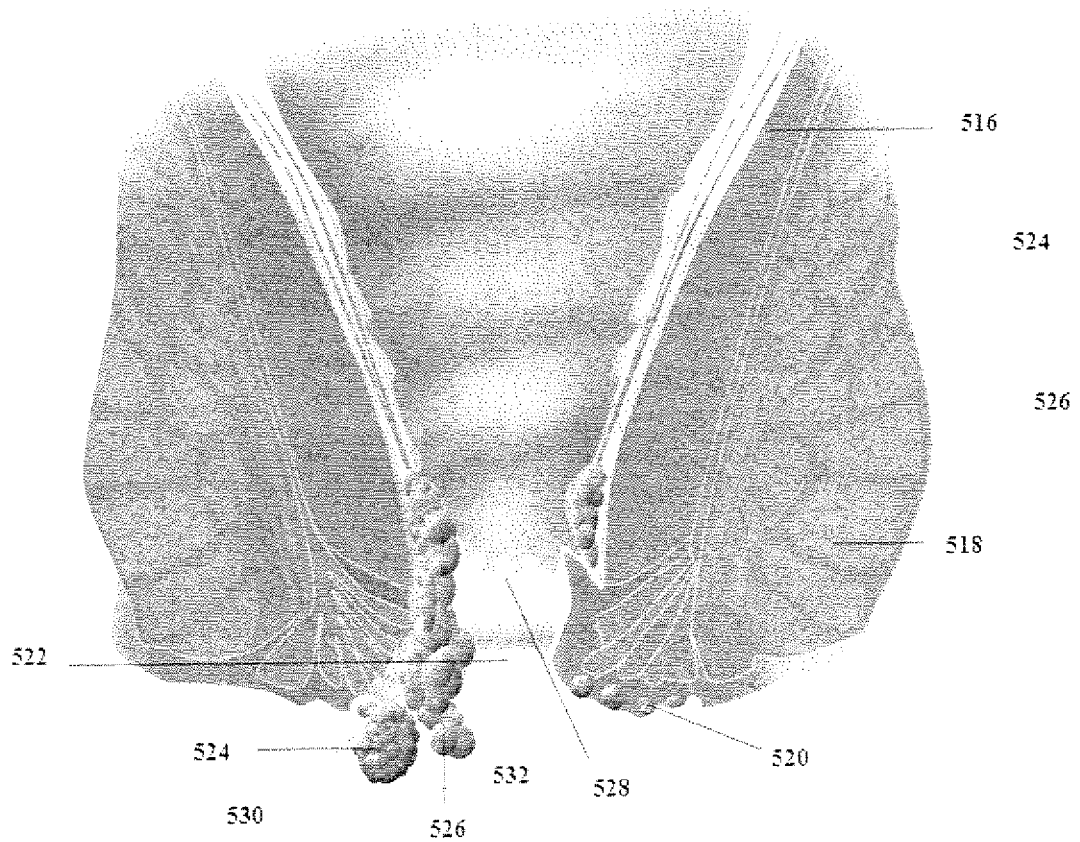
FIG. 5 anatomically illustrates two examples of possible injection or penetration ports.

FIG. 5 anatomically illustrates two examples of possible injection or penetration ports for fiber tip. Figure depicts internal anal sphincter 516, external anal sphincter 518, Perianal blood vessels 520, anoderm 522, external hemorrhoid 524, prolapsing internal hemorrhoid 526, and internal hemorrhoid pectinate line 528. Injection of the optical fiber can be carried out through the mucosa 530 or through the perianal skin 532.

In another embodiment, the device includes an intelligent system capable of measuring different geometrical parameters such as dimension of the pile or diameter and depths of target vessel and calculating the necessary laser energy parameters needed to shrink the pile or close target vessel.

The present invention is further illustrated by the following example, but is not limited thereby:

As an example, treatment system has a disposable or reusable hand-piece, which is composed of an anoscope and fiber optics used for treating the relevant hemorrhoidal cushion in the anal region. The patient is kept in lithotomy position and under general anesthesia. The anoscope is inserted into the anal canal of the patient with minimal discomfort. The target pile is pulled out by means of surgical instruments. Finally, laser is activated for 1-2 seconds as it enters the mucosa of the hemorrhoidal cushion to support entry and reduce bleedings from that entry port.

Following this, fiber tip is placed with the help of fiber's aiming beam which shines through the mucosa, or with digital (finger) control such that fiber lies in the center of the hemorrhoidal pile. Pile is irradiated at 5 to 20 W according to its size in either continuous or pulse mode. Pulse mode can be 3 seconds to start with the first pulse at the height of the base of the hemorrhoid and proceeding more distally by 3 mm steps. Each new location is accompanied by a pulse. The injection port can be re-used to address side region of the pile without the need for creating a new puncture. This results in total energies of 50 to 500 Joule per pile. A 20 MHz Doppler system with a 3 mm diameter probe assists in the location and position of the feeder artery branches which need to be treated by photocoagulation. The located arterial branches are irradiated in pulsed mode for a preset time interval. For example, 4 pulses of 1.3 seconds at 14 W are applied on each artery. Thus, total energy applied is approximately 70 J per hemorrhoidal branch. Then, complete closure of the vessel is monitored by the same Doppler system. Any accumulated blood or fluids from the site are removed during the procedure using aspiration means. Complete closure of each arterial branch supplying blood to the hemorrhoidal cushion is accomplished by photocoagulation and is confirmed by the Doppler image. After all hemorrhoidal arteries are confirmed to be photocoagulated, patient is kept in position and proctoscope is maintained inside anus. Then, next pile is addressed with the described means until all hemorrhoidal piles that need to be reduced are treated.

In another embodiment, original position of the hemorrhoidal cushions are reconstructed in case of immediate removal of all tissue compounds which irritate or disturb the sphincter apparatus before, in between and after individual sub-treatments. This method further comprises means for applying sutures starting 1-2 cm proximally from the dentate line and then proximally lifting the mucosal parts by applying a certain number of stitches to reconstruct the anatomy. Finally, lifting is finished by means of a deeper stitch through the rectum wall to use as a reliable anchorage suture and distally attaching all mucosal parts.

Described new invention offers the possibility to effectively treat mild and severe hemorrhoid conditions, rapidly, safely and minimizing disadvantages presented by prior art. Patients treated receive an integrated hemorrhoid treatment as both the cause (hemorrhoidal arteries) and symptoms (hemorrhoidal piles or cushions) are tackled using laser energy at low energy levels. Treatment success is substantiated with ultrasound imaging or Doppler ultrasound, so the possibility of recurrence is minimal.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A minimally invasive system for treating both the cause and symptoms of hemorrhoids, comprising:
   a radiation source;
   a handpiece;

a radiation distributing probe comprising a first channel and a second channel; said radiation distributing probe having a longitudinal axis and being rotatably connected to said handpiece;

an optical fiber connected to said radiation source and disposed in said first channel, said optical fiber comprising a distal tip directed perpendicularly to said longitudinal axis of said radiation distributing probe; and an imaging probe disposed in said second channel, said imaging probe comprising a distal tip configured to image perpendicularly to said longitudinal axis of said radiation distributing probe;

said radiation distributing probe comprising a manual locking mechanism disposed about said radiation distributing probe, said locking mechanism being configured to rotate with respect to said handpiece to lock said radiation distributing probe in only a first fixed rotational position or a second fixed rotational position whereby said radiation distributing probe is configured to rotate between only said first fixed rotational position and said second fixed rotational position with respect to said handpiece, said first fixed rotational position and said second fixed rotational position being 180 degrees from each other such that the positions of the distal tip of said optical fiber and the distal tip of said imaging probe are configured to be manually rotated 180 degrees to exactly switch places with each other without moving said handpiece.

2. The minimally invasive system according to claim 1, further comprising a viewing window for aiding location and treatment of hemorrhoids.

3. The minimally invasive system according to claim 1, wherein said handpiece features a visual distance scaling system to enable control of a safe treatment length.

4. The minimally invasive system according to claim 1, wherein the imaging probe is a Doppler ultrasound device.

5. The minimally invasive system according to claim 1 wherein said manually activated locking mechanism comprises a locking button disposed on the radiation distributing probe, and wherein said handpiece comprises two holes oriented radially at 180° to each other and configured to receive the locking button.

6. The minimally invasive system according to claim 1, wherein said radiation source comprises a diode laser operating at a wavelength capable of appropriately denaturizing/shrinking soft tissue, said diode laser being connected to said optical fiber's proximal end, wherein said optical fiber's distal end is configured to transmit laser energy towards tissue requiring treatment.

7. The minimally invasive system according to claim 6, wherein said optical fiber, connected to said laser, distributes the laser energy such that said treatment zone can be defined in diameter and shape as well as length.

8. The minimally invasive system according to claim 6, wherein said diode laser operates at a wavelength of 980+30 nm or 1470+60 nm.

9. The minimally invasive system according to claim 6, further comprising a viewing window to view an area under treatment.

10. A minimally invasive method of treating both the cause and symptoms of hemorrhoids in a patient using the system of claim 1 comprising the steps of:

a) inserting the handpiece and the radiation distributing probe into the anal canal of the patient, b) locating and isolating a particular hemorrhoidal pile with the imaging probe, c) without moving the handpiece, unlocking the manual locking mechanism, manually rotating, the radiation distributing probe 180 degrees to switch the places of the distal tip of the optical fiber and the distal tip of the imaging probe, locking the radiation distributing probe in place with the manual locking mechanism, and inserting said distal tip of id optical fiber into a mucosa of said particular hemorrhoidal pile and activating the laser source in order to submucosally irradiate said particular hemorrhoidal pile with laser energy according to its size, d) locating a vessel feeding a particular hemorrhoid cushion of aid particular hemorrhoidal pile with the imaging probe, e) unlocking the manual locking mechanism and manually rotating the radiation distributing probe 180 degrees to rotate said distal tip of said optical fiber 180 degrees into or onto said vessel feeding said, particular hemorrhoid cushion, locking the radiation distributing probe in place, and activating the laser source to irradiate and close said vessel under ultrasound monitoring, and f) repeating steps d) and e) for each of the vessels feeding said particular hemorrhoid cushion.

11. The method according to claim 10, further comprising a step of aspirating a treatment area to remove residual blood and debris between and after individual sub-treatments.

12. The method according to claim 10, further comprising a step of closing the vessels feeding said particular hemorrhoid cushion by means of suture ligation before, in between and after individual sub-treatments.

13. The method according to claim 10, further comprising a step of applying means for reconstructing the original position of said particular hemorrhoidal cushions in case of immediate removal of <all tissue compounds which irritate or disturb a sphincter apparatus before, in between and after individual sub-treatments.

14. The method according to claim 13, comprising means for applying sutures starting proximally from the dentate line and proceeding with a step of further proximally lifting the mucosal parts by applying a certain number of stitches to reconstruct original anatomy.

15. The method according to claim 14, further comprising a step of finishing said lifting by means of a stitch through the rectum wall to use as a reliable anchorage suture followed by the step of distally attaching all mucosal parts.

* * * * *